United States Patent [19]
Vandegriff et al.

[11] Patent Number: 5,873,894
[45] Date of Patent: Feb. 23, 1999

[54] DIAGNOSTIC TEST PROTOCOL IN AN IMPLANTABLE MEDICAL DEVICE

[75] Inventors: Joseph W. Vandegriff, Brazoria; Bryan J. Thome, Angleton, both of Tex.

[73] Assignee: Sulzer Intermedics Inc., Angleton, Tex.

[21] Appl. No.: 25,123

[22] Filed: Feb. 17, 1998

[51] Int. Cl.$^6$ .................................................. A61N 1/362
[52] U.S. Cl. ................................................................. 607/9
[58] Field of Search ..................................... 607/27, 32, 9

[56] References Cited

U.S. PATENT DOCUMENTS

| | | | |
|---|---|---|---|
| 5,312,445 | 5/1994 | Nappholz et al. | 607/9 |
| 5,395,396 | 3/1995 | Lindgren et al. | 607/9 |

*Primary Examiner*—William E. Kamm
*Attorney, Agent, or Firm*—John R. Merkling; Conley, Rose & Tayon

[57] ABSTRACT

An implantable medical device electrically stimulates the heart to beat and senses electrical activity in the heart. The medical device generally includes a processor, a plurality of electrodes, and a sense amplifier. The medical device is capable of performing a variety of diagnostic tests, such as a sensing test in which a suitable sensitivity setting is computed for the sense amplifier. An external programmer is also provided to initiate the diagnostic tests. The programmer transmits a start signal to the implantable medical device and the medical device's processor initiates the diagnostic test specified by the programmer via the start signal. The implantable device is capable of completing the diagnostic test without further communication from the programmer or may initiate communication with the programmer during a refractory period in which signals from the programmer will not interfere with the diagnostic test. In the latter case, the programmer responds before the refractory period ends.

25 Claims, 4 Drawing Sheets

DIAGNOSTIC TEST PROTOCOL IN AN IMPLANTABLE MEDICAL DEVICE

BACKGROUND OF THE INVENTION

1. Field of the Invention

The present invention relates generally to cardiac stimulating devices. More particularly, the present invention relates to an improved protocol for a diagnostic test performed by an implantable medical device.

2. Description of the Related Art

In the normal human heart, illustrated in FIG. 1, the sinus (or sinoatrial (SA)) node, which is generally located near the junction of the superior vena cava and the right atrium, constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called "rhythmicity", or "automaticity." Certain other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly labeled) is a medical device which delivers electrical pulses to an electrode that is implanted adjacent to or in the patient's heart in order to stimulate the heart's SA node so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Pacers today are typically designed to operate using one of three different response methodologies, namely, asynchronous (fixed rate), inhibited (stimulus generated in the absence of a specified cardiac activity), or triggered (stimulus delivered in response to a specified parameter). Broadly speaking, the inhibited pacemakers are "demand" type pacemakers, in which a pacing pulse is only generated when demanded by the heart. To determine when the heart requires pacing, demand pacemakers may sense various conditions such as heart rate, physical exertion, temperature, and the like. Moreover, pacemaker implementations range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Because of the large number of options available for pacer operation, an industry convention has been established whereby specific pacer configurations are identified according to a code comprising three or four letters. A fifth coded position may be used to describe a pacemaker's ability to respond to abnormally high heart rates (referred to as tachycardia). Because most pacemakers do not provide any antitachycardia functions, the fifth coded position is not used in most commonly used pacemaker types. Thus, most common configuration codes comprise either three or four letters, as shown in Table I below. For this reason and for simplicity's sake, the fifth code position is omitted from the following table. Each code can be interpreted as follows:

TABLE I

| Code position | 1 | 2 | 3 | 4 |
|---|---|---|---|---|
| Function Identified | chamber paced | chamber sensed | response to sensing | programmability, rate modulation |
| Options Available | 0—none<br>A—atrium<br>V—ventricle<br>D—dual<br>(A + V) | 0—none<br>A—atrium<br>V—ventricle<br>D—dual<br>(A + V) | 0—none<br>T—triggered<br>I—inhibited<br>D—dual<br>(T + I) | 0—none<br>P—programmable<br>M—multi-programmable<br>C—communicating<br>R—rate modulating |

For example, a DDD pacer paces both chambers (atrium or ventricle) and senses in both either chambers. Thus, a pacer in DDD mode, may pace the ventricle in response to electrical activity sensed in the atrium. A VVI pacer paces and senses in the ventricle, but its pacing can be inhibited by spontaneous electrical activation of the ventricle (i.e., the ventricle paces itself naturally). In VVIR mode, ventricular pacing is similarly inhibited upon determining that the ventricle is naturally contracting. With the VVIR mode, the pacer's pacing rate, however, in the absence of naturally occurring pacing, is modulated by the physical activity level of the patient. Pacers commonly include accelerometers to provide an indication of the patient's level of physical activity.

As illustrated in the table above, it may be desired to sense in one cardiac chamber (i.e., detect electrical activity representative of contraction of the chamber and referred to as a "sensed event") and, in response, pace (referred to as a "paced event") in the same or a different chamber. In general, most pacemakers today incorporate a sensing function to detect electrical activity at the site of one or more electrodes. The sensing circuit in the pacemaker (often referred to as the "sense" circuit) receives the electrical signals from the electrodes and determines when a physiologically significant event as occurred. Accordingly, if the heart's natural pacemaker is able to stimulate the heart to beat properly, the pacemaker's sense circuit detects the naturally occurring electrical impulses and determines that the heart does not require artificial stimulation.

Most pacemaker sense circuits incorporate an amplifier that amplifies the electrical signals received from the electrodes. Sense circuits typically also incorporate, or are coupled to, a comparator circuit that compares the magnitude of the amplified signal from an electrode to a reference signal. When the amplified signal from the electrode exceeds the amplitude of the reference signal, the pacemaker determines that a physiologically significant event has occurred. In this context, the physiologically significant events are cardiac events. It is important for a pacemaker to accurately determine when a cardiac event has occurred. This means that the pacemaker should detect a true cardiac event, but not respond to non-cardiac signals.

The sense circuit's ability to accurately determine when a cardiac significant event has occurred may be compromised because the electrodes are sensitive to various sources of electrical signals. For example, muscle tissue generates electrical signals referred to as electromyogram ("EMG") signals. These EMG signals may be picked up by the pacemaker electrodes and amplified along with the naturally occurring cardiac signals. By way of further example, electromagnetic interference (EMI) signals generated outside the patient's body may also be detected by the pacemaker's electrodes.

For a sense circuit to accurately respond to cardiac signals, the circuit's sensitivity must be set at an optimal level. That is, the sensitivity must be set high enough so that all cardiac events will be detected, but not so high that other non-cardiac related events are detected and falsely determined to have a cardiac origin. Thus, upon implantation into the body, the surgeon monitors the pacemaker and sets its sensitivity appropriately.

A physician may also monitor the pacemaker during post-operative examinations. During such an examination, the physician may determine if the sensitivity of the pacemaker's sense circuit is set correctly, or needs to be reset. Most pacemakers are capable of performing a sensitivity test that is initiated by an external programmer controlled by the physician. The programmer includes a "wand" that is positioned over the site on the chest in which the pacemaker is implanted. Using any one of a variety of wireless communication techniques, commands and data can be transmitted between the implanted pacemaker and the wand. Using the external programmer, the physician can command the pacemaker to begin a sensing test. During the test, the pacemaker's sense circuit monitors the heart's naturally occurring electrical rhythm and generates data based on the amplitude of the heart's signal relative to the internal reference signal. The programmer periodically transmits a command to the pacemaker directing the pacemaker to transmit the data to the programmer. The programmer analyses this data to compute an incremental change to the sensitivity setting and transmits the newly computed sensitivity setting back to the pacemaker. The programmer also analyzes the data provided by the pacemaker to determine if the previously transmitted sensitivity setting was optimal. Once the external programmer determines that the sensitivity of the pacemaker is at an optimal setting, the programmer terminates the sensing test. The external programmer includes sufficient data storage and processing capability to receive the sensing test data and calculate new sensitivity settings.

Unfortunately, the signals that the external programmer repeatedly transmits during the sensing test may interfere with the accuracy of the test itself. The implanted pacemaker's electrodes are sensitive to any electrical signal in the vicinity of the electrode, and thus the electrodes may pick up the command and sensitivity signals that are being transmitted to the pacemaker by the programmer. The programmer's signals combine with the heart's naturally occurring cardiac signals and are provided to the sense circuit via the electrodes. All signals impinging on the electrodes, including any control and data signals generated by the external programmer are processed by the pacemaker (and thus the programmer) during the sensing test. The programmer will compute new sensitivity values based on data that has been distorted by the programmer itself. Thus, if programmer-initiated signals are processed by the pacemaker during the sensing test, the accuracy of the test itself is detrimentally effected. In other words, the very device that is employed to initiate and control the sensing test (i.e., the external programmer) introduces errors into the test.

For these reasons, an implantable medical device is needed that can perform a sensing test without introducing errors into the test from control signals transmitted from the programmer to the pacemaker during the test. Despite the advantages such a device would provide, no such device is known to exist today.

SUMMARY OF THE INVENTION

Accordingly, there is herein provided an implantable medical device, such as a pacemaker or implantable cardioverter/defibrillator, that electrically stimulates the heart to beat and senses electrical activity in the heart. The medical device generally includes a processor, a plurality of electrodes, and a sense amplifier. The medical device is capable of performing a variety of diagnostic tests. For example, the medical device may perform a sensing test in which a suitable sensitivity setting is computed for the sense amplifier.

An external programmer is used to initiate the diagnostic tests. The programmer transmits a start signal to the implantable medical device and the medical device's processor begins the diagnostic test specified by the programmer. In one embodiment of the invention, the medical device is capable of completing the diagnostic test without further communication from the programmer. This eliminates the potential for control and data signals transmitted by the programmer from interfering with the diagnostic test being performed by the implantable device.

In an alternative embodiment, the implantable medical device transmits a status signal to the external programmer during a refractory period of time that follows a cardiac event. The implantable device preferably transmits the status signal as near to the beginning of the refractory period as possible. The status signal includes information regarding the status of the implantable device and the diagnostic test being performed. For example, if the implantable device is performing a sensing test, the status signal includes the current sensitivity setting computed by the implantable device's processor. Preferably before the refractory period expires, the programmer transmits a return signal to the implantable device so that the implantable device will know the programmer is still active. The refractory period may be fixed or programmable, and normally is about 200 milliseconds. During the refractory period, the implantable device will not detect cardiac events; either the device's sensing capability is turned off or its output is ignored by the processor. By transmitting signals to the implantable device only during the refractory period, the external programmer will not interfere with the accuracy of the diagnostic tests.

Pacing support for the patient can be compromised during a diagnostic test. Thus, the return signal transmitted by the programmer also causes the implantable medical device to reset a communication counter. If the implantable device does not timely receive the programmer's return signal and does not reset the communication counter, the counter will expire, causing the pacer's processor to terminate the diagnostic test. This permits the implantable device to return promptly to its normal pacing mode without programmer assistance.

BRIEF DESCRIPTION OF THE DRAWINGS

For a detailed description of the preferred embodiment of the invention, reference will now be made to the accompanying drawings, wherein.

DETAILED DESCRIPTION OF THE PREFERRED EMBODIMENTS

Figure 1:
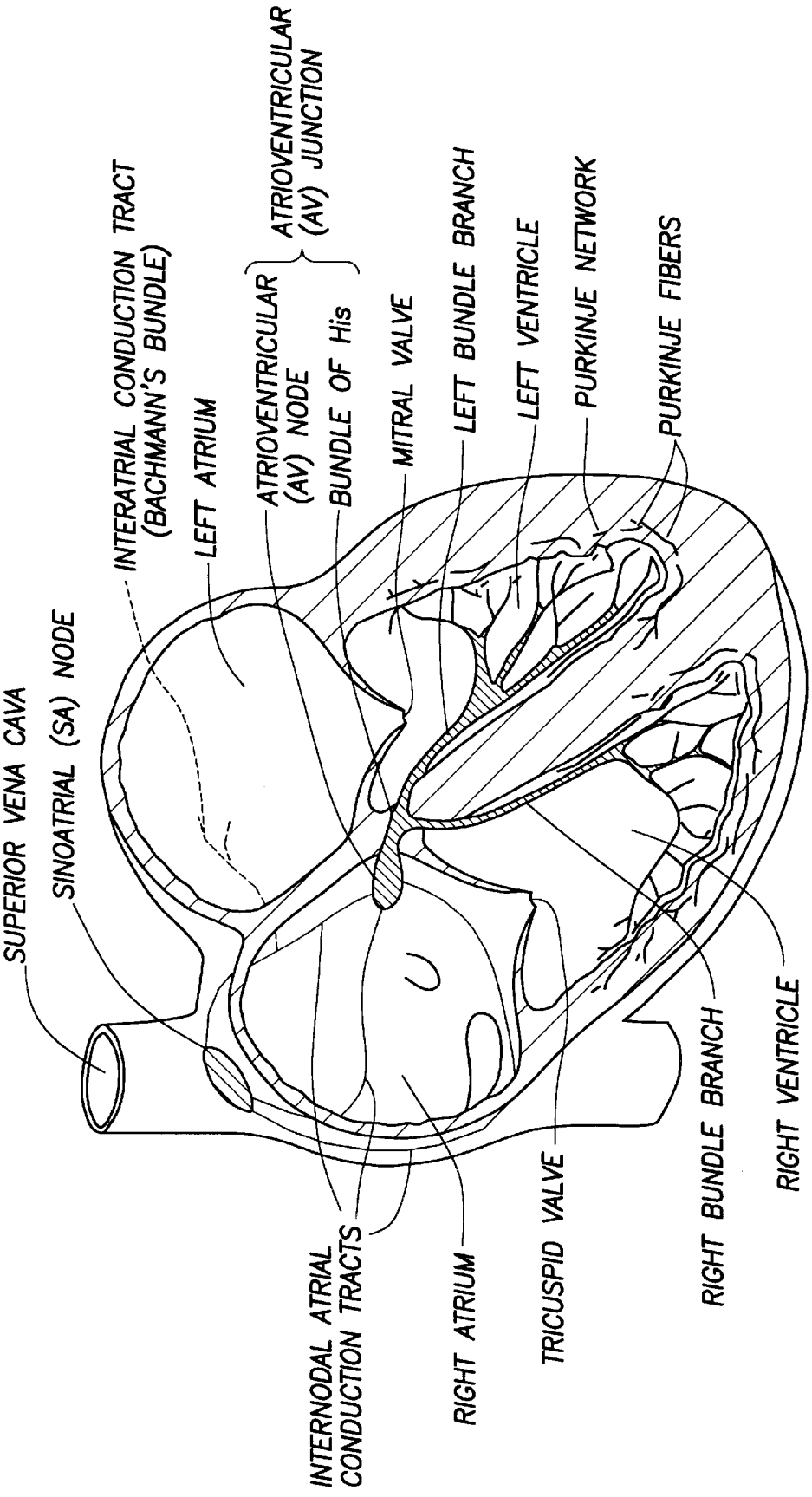
FIG. 1 is a schematic cut-away view of a human heart, in which the various relevant parts are labeled.
Figure 2:
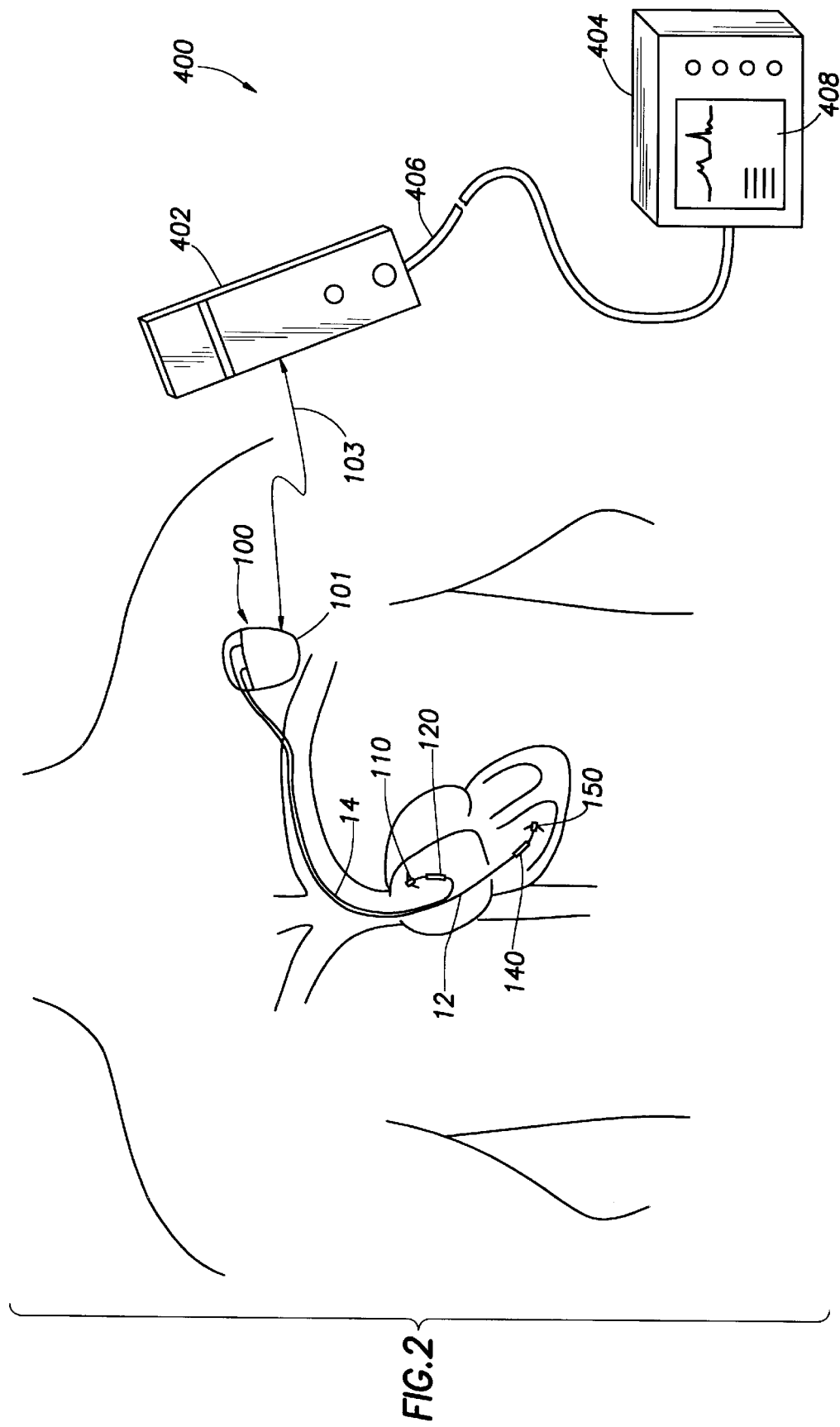
FIG. 2 is a schematic diagram of an implanted pacemaker and external programmer constructed in accordance with the present invention.

Referring now to FIG. 2, an implantable medical device 100 constructed in accordance with the preferred embodiment of the invention is shown implanted in a human body and coupled, in an exemplary configuration, to the patient's heart by leads 12, 14. Medical device 100 also communicates with an external programmer 400. The implantable medical device 100 may include a pacemaker or any medical device that performs pacing functions, including some defibrillators. For purposes of describing the preferred embodiments of the invention, however, the implantable medical device 100 will hereafter be described as an implantable pacemaker or simply "pacer." However, it should be understood that the invention may be employed in any of a variety of implantable medical devices besides pacemakers, such as defibrillators.

The electrode arrangement shown in FIG. 2 represents a dual chamber pacing configuration in which two leads 12 and 14 are coupled to the pacer 100. In the configuration shown, the leads are positioned in two chambers of the heart, lead 12 being implanted in the right ventricle and lead 14 being implanted in the right atrium. In the present invention, each lead may incorporate any desired number of electrodes. The leads 12, 14 shown in FIG. 2, for example, are bipolar leads meaning each lead includes two electrodes. Lead 14 includes a tip cathode electrode 110 and a ring anode electrode 120. Lead 12 includes a tip cathode electrode 150 and a ring anode electrode 140. As one skilled in the art will understand, two, three, and four lead devices all have been used or suggested as various prior art pacemaker configuration schemes, and may also be employed in the present invention. Further, the pacemaker housing or "can" 101 itself can be used as an electrode. Thus, the lead and electrode configuration shown in FIG. 2 is intended to be merely exemplary of the many configurations that are possible for use in the present invention.

Regardless of the lead and electrode configuration implemented, a communication link exists between the pacer 100 and the external programmer 400. The programmer 400 generally includes a hand-held "wand" 402 connected to a control unit 404 via an umbilical cable 406. The control unit 404 includes a display 408 through which a physician or medical technician can view status and data related to the pacer 100. After positioning the wand 402 on or near the patient's skin over the site of the implanted pacer 100, the programmer 400 is activated by the medical professional to establish communication with the pacer. Subsequently, control and data signals 103 may be transmitted bidirectionally between the pacer 100 and programmer 400.

Figure 3:
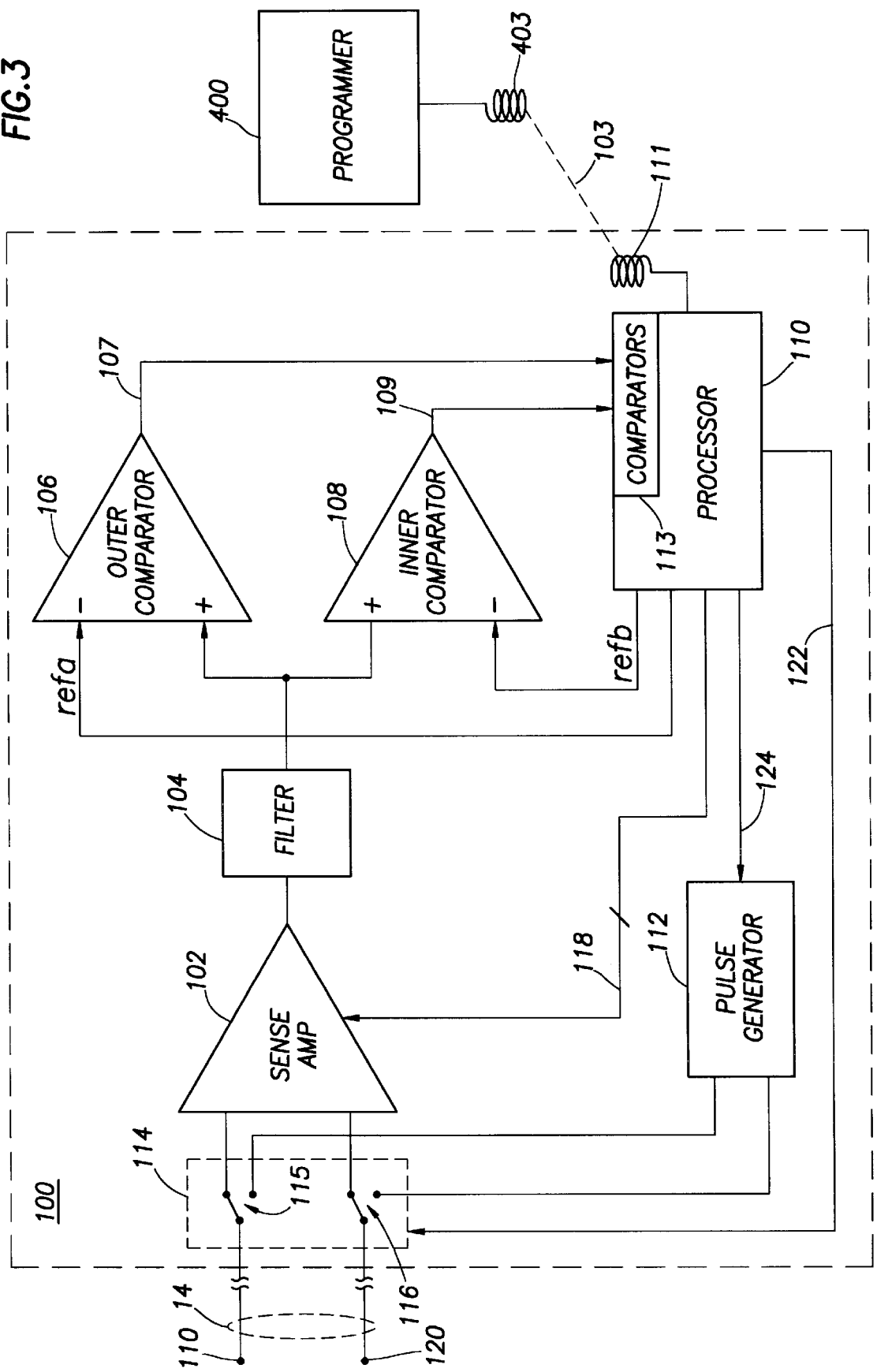
FIG. 3 is a block diagram of the pacemaker of FIG. 2 in accordance with a preferred embodiment.

Any one of a number of communication techniques may be implemented for establishing the communication link between the pacer 100 and programmer 400. In accordance with a preferred embodiment, however, the communication link is created by means of a pair of coils of wire (shown in FIG. 3 as 111, 403). Referring to FIG. 3, coil 111 is coupled to and may be contained within the implanted pacer 100. Coil 403 is contained within wand 402 of external programmer 400. An alternating current generated in one coil creates electromagnetic waves that, in turn, induce a current in the other coil. Information is transmitted via the electromagnetic waves by modulating the current in the transmitting coil in accordance with a predetermined modulation technique. An exemplary communication technique is described in detail in U.S. Pat. No. 5,314,453, incorporated herein by reference.

Electromagnetic signals transmitted from the wand 402 through the body to the pacer 100 may also impinge on the leads 12, 14 and induce currents in the leads. Nevertheless, because of the features of the present invention that are described in detail below, even if a diagnostic test, such as a sensing test, is underway when signals from the wand 402, intended for the receiving coil 111 in the pacer 100, are picked up by the leads 12, 14, the accuracy of the sensing test is not detrimentally effected.

Referring still to FIG. 3, the components of the pacer 100 particularly relevant to the invention generally include a sense amplifier 102, a filter 104, an outer comparator 106, an inner comparator 108, a processor 110, a pulse generator 112, and a switch unit 114. It should be recognized that pacer 100 may include other components that are not specifically shown in FIG. 3. Further, the embodiment of the invention shown in FIG. 3 is illustrated with respect to electrodes 110 and 120 of lead 14, but may include additional electrodes such as electrodes 140, 150 of lead 12 (FIG. 2). Additional sense amplifiers 102, filters 104 and comparators 106, 108 also may be desired as the number of electrodes employed increases.

The sense circuit of the pacer 100 generally includes the sense amplifier 102, filter 104 and outer and inner comparators 106, 108. These components function to amplify and condition the signals received from electrodes 110, 120 on lead 14. Sense amplifier 102 preferably is a low power amplifier operating from a power supply of approximately one microampere of current. A suitable sense amplifier is disclosed in U.S. Pat. No. 4,913,145, incorporated herein by reference.

Filter 104 preferably is a band pass filter implemented as a switched capacitor configuration. Band pass filter 104 generally passes signals from its input terminal to its output terminal whose frequencies are within a predetermined range (or "band") of frequencies, and attenuates signals whose frequencies are outside the filter's frequency band. Filter 104 processes the amplified signal by attenuating those frequencies that are known not to include relevant cardiac signals. Filter 104, however, generally cannot attenuate non-cardiac signals whose frequencies are within the filter's frequency band. An example of a suitable filter is described in U.S. Pat. No. 5,024,221, incorporated herein by reference, although any other low power, reliable filter suitable for use in implantable pacemakers may also be employed in the invention.

Comparators 106, 108 preferably are also low power devices, such as that described in U.S. Pat. No. 4,913,145, incorporated herein by reference. Each comparator compares the voltage provided to it on its non-inverting (+) terminal with the voltage on its inverting (-) terminal. Each comparator 106, 108 generates a logic high output signal on its output line 107 or 109 respectively if the non-inverting (+) input voltage is greater than the inverting (-) voltage. Conversely, comparators 106, 108 generate a logic low output signal on their respective output lines 107, 109 if the inverting (-) voltage is greater than the non-inverting (+) voltage. Reference voltages refa and refb are provided to the inverting terminals of comparators 106 and 108, respectively, from processor 110 and represent target thresholds as explained below.

The processor 110 preferably controls the operation of pacer 100 and may include any suitable controller or processor such as the Intel 8051 or a custom processor. The processor 110 preferably receives input signals from the comparators 106, 108 over signal lines 107, 109, controls the sensitivity setting of the sense amplifier 102 via control lines 118, controls the configuration of switch unit 114 via control lines 122, and determines when a pacing pulse should be delivered from the pulse generator 112 through the electrodes to the heart.

Pulse generator 112 generally includes suitable circuitry to generate an electrical pulse that has sufficient energy to cause a desired cardiac chamber to contract. Accordingly, pulse generator 112 generates a voltage pulse whose amplitude and time duration is approximately 3.5 volts and 0.45 milliseconds, respectively. The pulse generator 112 may also include a pacing rate limiter for safety to ensure that the processor 110 does not erroneously attempt to pace the heart at an excessively high rate.

Referring still to FIG. 3, the switch unit 114 includes one or more switches coupling the electrodes 110, 120 to either the sense amplifier 102 or the pulse generator 112. As shown, switch unit 114 includes switch 115 and 116. Switches 115 and 116 preferably are implemented as solid state devices, such as field effect transistors (FET's). Switch 115 couples electrode 110 to either the sense amplifier 102 or pulse generator 112, and switch 116 couples electrode 120 to either the sense amplifier or pulse generator 112. The state of the switches is controlled from the processor 110 via a control signal on line 122.

At times when the pacer 100 has been programmed to sense the electrical activity present on electrodes 110 and 120, the processor 110 switches the states of switches 115 and 116 to the states shown in FIG. 3 so that the electrodes connect to the sense amplifier 102. Sense amplifier 102 amplifies the voltage level detected at the electrodes and provides the amplified signal to the filter 104. In turn, the filtered signal is provided to the non-inverting (+) terminals of both comparators 106, 108. These comparators provide their logic high or low output signals on lines 107, 109 to processor 110. Processor 110 interprets the comparator signals on line 107, 109 to determine if a cardiac event has occurred.

When processor 110 is to pace the heart, the switches 115 and 116 are switched to the alternative states from that shown in FIG. 3 in which the electrodes 110 and 120 connect to the pulse generator 112. A signal on line 124 from the processor 110 to the pulse generator 112 directs the pulse generator to generate a pacing pulse to be provided through switch unit 114 to the heart via electrodes 110 and 120.

The communication link 103 between the implanted pacer 100 and external programmer 400 is illustrated schematically in FIG. 3 between coils 111 and 403. Coil 111 is contained within, or otherwise connected to, the implanted pacer 100, and coil 403 is contained on or within the wand 402 (FIG. 2). Communication preferably is bidirectional. That is, data and/or control signals may be transmitted from the programmer 400 to the pacer 100 and from the pacer to the programmer.

The invention is particularly useful when the pacer 100 is sensing cardiac activity and, at the same time, the possibility exists that an external programmer may attempt to transmit a signal to the pacer and thus disrupt the accuracy of the sensing cycle. One such possible scenario is a sensing test during which the pacer senses and processes the voltage on the electrodes implanted in the heart. Although the preferred embodiments described below are illustrated with respect to a sensing test, the principles described easily can be employed with other types of diagnostic tests and pacer activity involving programmer communication with the pacer.

Before describing the improved communication protocol provided by the present invention, the sensing test will first be described with reference to FIGS. 3 and 4. As stated previously, the goal of the sensing test is to determine the optimal sensitivity setting for the pacer's sense circuit. The target reference voltage levels, refa and refb preferably are set at different voltage levels with respect to ground (0 volts). The reference voltages refa, refb may be either fixed or programmable. If programmable, the processor 110 programs the voltage levels of the references.

Figure 4:
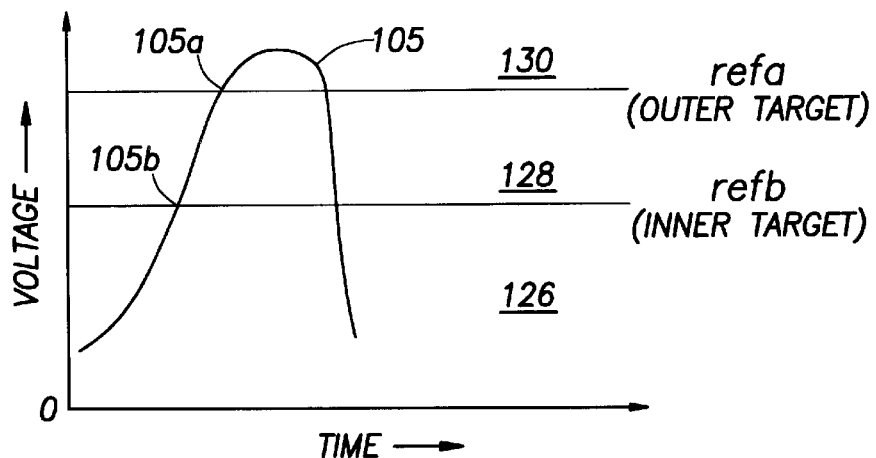
FIG. 4 is an exemplary cardiac signal monitored during a sensing test of the pacemaker of FIG. 2.

A portion of an exemplary cardiac signal 105 also is shown in FIG. 4. This signal represents the amplified cardiac signal provided by sense amplifier 102 through the filter 104 to the comparators 106, 108. Thus, cardiac signal 105 represents the signal appearing on the non-inventing (+) terminals of comparators 106, 108. In general, the magnitude of any cardiac signal varies with respect to time. The exemplary amplified cardiac signal 105 in FIG. 4 exceeds the refb target reference at point 105b and the refa target reference at point 105a. The refb reference is associated with the inner comparator 108 and the refa reference is associated with the outer comparator 106. Thus, at point 105b (the point at which the cardiac signal exceeds the inner comparator's reference signal refb, the cardiac signal is said to have "crossed the inner target." Likewise, the cardiac signal 105 "crosses the outer target" at point 105a.

The amplitude of the cardiac signal 105 of FIG. 4 can be divided into three ranges. Range 126 corresponds to a cardiac signal amplitude that is less than target refb. Range 128 corresponds to a cardiac signal amplitude that is between targets refa and refb and range 130 corresponds to a cardiac signal amplitude that exceeds target refa. The goal of the sensing test is to set the sensitivity of the pacer's sense circuit so that the amplified cardiac signal 105 is just barely in range 130 (i.e., the amplitude just crosses the outer target by less than a relatively small voltage range). A higher sensitivity setting will make the sense circuit too sensitive to lower amplitude noise, and a lower sensitivity setting may cause the sense circuit not to detect true cardiac events. It should be apparent from FIG. 4 that one of three scenarios is possible for the peak amplitude of the cardiac signal 105: (1) neither target is crossed (range 126); (2) only the inner target, refb, is crossed (range 128); or (3) the outer target, refa, is crossed. Obviously, for the third scenario in which the outer target is crossed, the inner target necessarily is also crossed. For purposes of this disclosure, a cardiac signal that crosses the outer target is understood to also have crossed the inner target.

The sensing test protocol determines to which range the amplitude of the cardiac signal 105 corresponds (ranges 126, 128, or 130). This determination is made by monitoring the cardiac signal over a succession of heart beats and recording the number of times the cardiac signal 105 crosses the targets, refa and refb. In accordance with the preferred embodiment, the range to be assigned to a particular signal is determined by the first comparator whose target is crossed three times. Thus, if the outer comparator target (refa) is crossed three times before just the inner target (refb) is crossed, the cardiac signal's peak amplitude is determined to be in range 130. If only the inner target (refb) is crossed three times before the outer target is crossed, the peak amplitude of the cardiac signal is determined to be in range 128. Finally, the peak cardiac signal amplitude is determined to be in range 126 if neither comparator is crossed for three heart beats. It should be apparent that only knowing the range corresponding to the cardiac signal does not provide information as to absolute magnitude of the cardiac signal. For example, simply knowing that the outer target has been crossed by the cardiac signal 105 does not indicate how far above target refa the cardiac signal reached. Further discussion of this sensing test protocol is provided in the *Physician's Manual, MarathonTM Cardiac Pulse Generator*, page 54, Intermedics (1996), incorporated herein by reference.

In previous pacer/programmer systems, the implanted pacer transmits the inner and outer comparators' output signals to the external programmer. The external programmer includes a pair of counters, one for the inner comparator and another for the outer comparator. The counters increment each time the associated comparator target reference signal is crossed. The range corresponding to the peak amplitude of the cardiac signal is thus determined by the counter that counts from zero to three (or down from three to zero) first in accordance with the methodology described above. If the cardiac signal is determined to be in range 130, the sensitivity setting of the pacer is too high, and the external programmer incrementally reduces the sensitivity level and transmits the new sensitivity setting to the pacer and the above process is repeated. Once the cardiac signal is determined to be in range 128, the sensitivity setting is adjusted upward so that the amplified cardiac signal generally just exceeds the outer target. At this point, the sensitivity setting is optimal and the sensing test ends. It should be noted that the sensitivity setting must be incrementally changed because the absolute magnitude of the cardiac signal is not known.

In accordance with the preferred embodiment of the invention shown in FIG. 3, the implantable pacer 100 includes counters 113 and computes new sensitivity settings itself, rather than relying on the external programmer to calculate new sensitivity settings and transmitting those settings back to the pacer. The counters preferably are implemented in software executed by processor 110, but may also be implemented with known, discrete circuit elements (not specifically shown). Reducing the amount of communication traffic between the programmer and pacer (and in particular communications from the programmer to the pacer) advantageously reduces the risk of a control signal from the programmer interfering with the accuracy of the sensing test performed by the pacer.

Eliminating communication altogether between the implanted pacer and external programmer, however, may not always be desired. While the pacer is performing the sensing test, pacing support for the patient is compromised. The pacer's pacing rate must be reduced so that the sense circuit can sense the patient's naturally occurring intrinsic cardiac rhythm, rather than the pacing signals that are generated by the pacer. Because the pacing support for the patient is compromised during the sensing test, the sensing test should be terminated as quickly as possible so that the pacer can return to its normal pacing mode of operation. Accordingly, the test should end if power is turned off to the programmer or the wand is removed from the patient's chest. Another factor should also be taken into account. Physicians generally prefer to monitor the status of the pacer during the sensing test. Physicians desire to know the current sensitivity setting of the pacer's sense circuit as a function of time during the sensing test.

To accommodate these concerns, an alternative preferred embodiment of the pacer 100 periodically transmits a self-generated communication ("SGC") signal. The SGC signal generally includes a frame (or multiple frames) of data that encode various parameters. Each frame comprises a series of bytes of data in accordance with a suitable communication protocol. One of the parameters encoded in the SGC frame from pacer 100 is the current sensitivity setting of the sense amplifier 102 (FIG. 3) as computed by the processor 110. Alternatively, this parameter may include an index value to a table of sensitivity values that is stored in the programmer 400. If this is the case, the programmer 400 uses the index value to look up or retrieve the sensitivity value from the table. Regardless of how the current sensitivity settings are provided to the external programmer 400, the sensitivity setting is displayed to the physician either graphically or in tabular form on the display 408 of programmer 400. Other parameters relevant to the status of the sensing test and the pacer 100 may also be included in the SWRT frame.

Many present day pacemakers are configured and implanted to both sense and pace. Such pacemakers usually disable their sensing function (or at least ignore any signals from the sense circuit) during a predetermined period of time following either a naturally occurring heart beat or a pacemaker induced paced beat. This period of time during which sensing is disabled is referred to as the "refractory" period. The refractory period is beneficial to prevent the pacer from inappropriately responding to certain electrical signals that may be sensed by the sense circuit during the refractory period. This is best understood by reference to a dual chamber pacer such as that illustrated in FIG. 2. Such a pacer may sense electrical activity in the right atrium, but pace in the right ventricle. After a ventricular pace, various electrical signals from the ventricle may propagate to the right atrium and impinge on the atrial electrodes 110, 120. These ventricular-based signals include the ventricular pacing pulse generated by the pacer itself, far field R-waves caused by the depolarization of the ventricular muscle mass, and retrogradedly conducted activity caused by electrical conduction from the ventricle. This collection of various signals commonly occurs during the refractory time period immediately following a ventricular beat. It is generally preferred for the pacer not to respond to these signals. For this reason, the pacer's sense circuit typically is disable (or ignored by the processor) during the refractory period following a sensed event.

In the present invention, during the refractory period, and preferably as near to the beginning of the period as possible, the pacer 100 transmits the SGC frame to the external programmer 400. In response to receiving the SGC, the programmer 400 transmits back to the pacer 100 a return signal from which the pacer determines that the programmer 400 is still active and that the wand 402 is in place on the patient's chest.

The pacer 100 maintains a communication counter (not specifically shown) that preferably is implemented in software executed by the processor 110. The communication counter either counts up from zero to a predetermined value or down from the predetermined value to zero. In either event, once the communication counter expires, the pacer 100 terminates the sensing test and returns to its normal pacing mode of operation. To prevent the sensing test from terminating early, the signal returned by the programmer 400 to the pacer 100 upon receiving the pacer's SGC frame resets the pacers communication counter. Thus, as long as the programmer's wand 402 is positioned correctly on the patient's chest and the programmer 400 is active and properly functioning, the pacer's communication counter will not expire during the sensing test, allowing the test to continue until completion.

The signal returned from the programmer 400 to the pacer 100 preferably is generated by the programmer and transmitted to the pacer before the refractory period of the current cardiac cycle ends. Because the pacer's sense circuit is disabled (or ignored by the processor 110) during the refractory period, the return signal from the programmer will not detrimentally effect the sensing test, as commonly occurs with many previous pacer/programmer systems. The refractory period can be fixed or programmable. It is generally believed that a refractory period of 100 milliseconds (0.1 seconds) is suitable for most patients, but other refractory time periods may also be used.

It should be recognized that, although the programmer's return signal is transmitted during the refractory period, the signal could also be transmitted after the refractory period expires. In that situation, however, the programmer's return signal may interfere with the sensing test. Once the pacer 100 completes the sensing test, the pacer preferably discontinues the transmission of SGC frames to the programmer.

Figure 5:
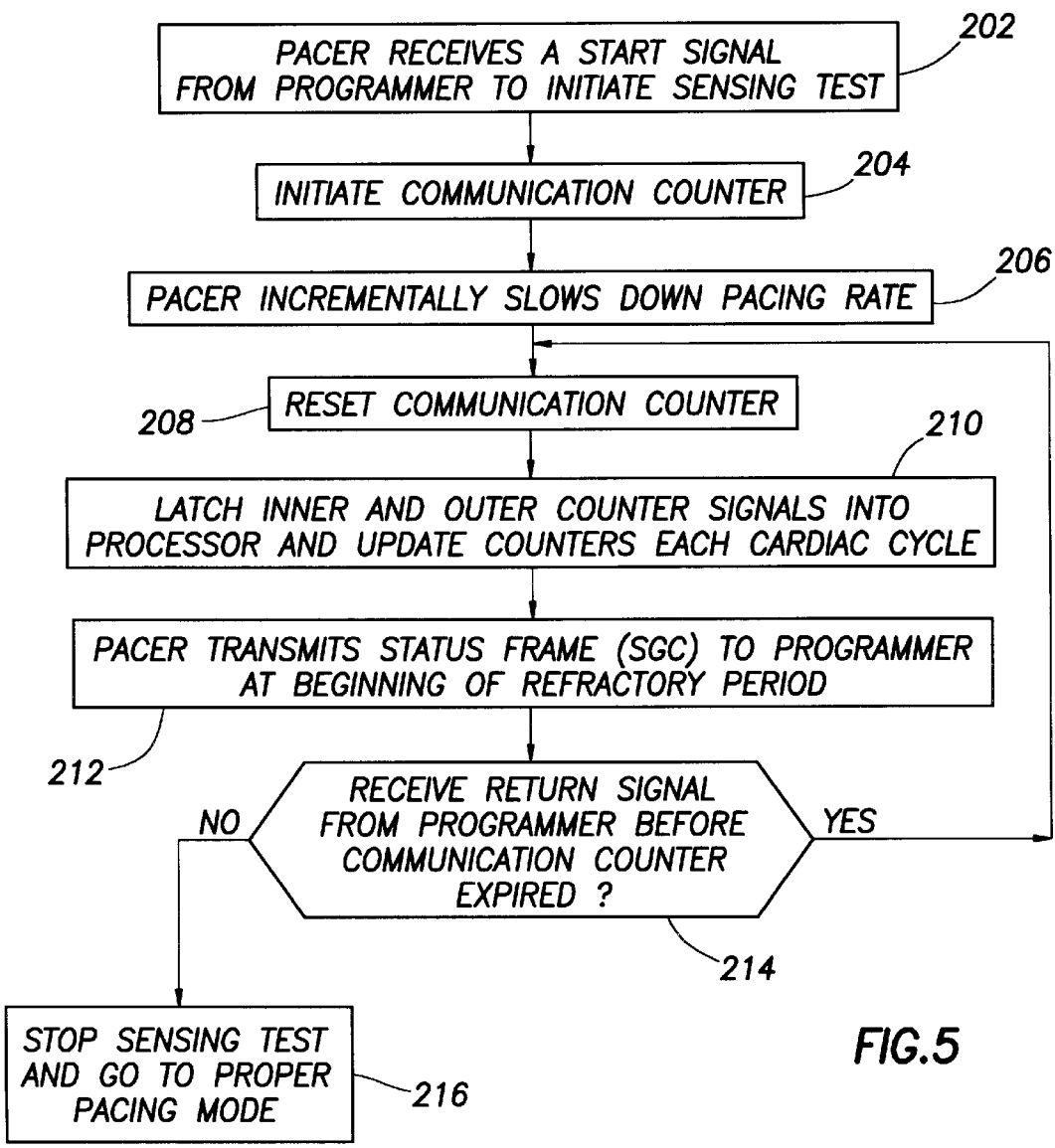
FIG. 5 is a flow diagram of a method for performing a sensing test in accordance with a the pacemaker and external programmer of FIG. 2.

The preferred communication protocol is further illustrated with respect to the logic flow diagram 200 of FIG. 5. The logic flow 200 only illustrates the communication protocol, and not the logic implemented by the pacer to calculate new sensitivity settings. The external programmer 400 initiates the sensing test in step 202 by transmitting a start signal to the pacer 100. In step 204 the programmer 100 initiates the pacer's communication counter. To transition between the current pacing mode of operation to the sensing test mode (during which little pacing support is provided by the pacer) with as little discomfort to the patient as possible, the pacer incrementally slows down the pacing rate in step 206. In step 208, the communication counter is reset. In step 210, the pacer latches the output signals from the inner and outer comparators 106, 108 into the processor 110, and increments the counters associated with each comparator for each cardiac cycle. During each cardiac cycle, the pacer 100 also transmits a SGC frame at the beginning of the refractory period to the external programmer 400 (step 212). If the pacer 100 receives the return signal from the programmer 400 before the communication counter expires (determined by decision step 214), the pacer resets the communication counter in step 208 and returns to step 210. The sensing test continues in this fashion until either the test is completed and terminates according to its own predetermined protocol (this step is not specifically shown in FIG. 5) or the communication counter expires in step 216.

The preferred embodiments described above illustrate the benefits of the present invention. Most significantly, the invention permits data communication between an implanted pacer and an external programmer during a sensing or other test without the risk of the communication signals interfering with the test.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A medical device adapted to be implanted in the human body for electrically stimulating the heart and for sensing electrical activity in the heart, the device comprising:
    a communication unit that permits communication between the medical device and a programmer;
    at least one electrode adapted to be coupled to the heart;
    a sense amplifier electrically coupled to said electrode, said sense amplifier receiving an electrical signal from said electrode and generating an amplified signal;
    a processor coupled to said sense amplifier and effective to initiate a refractory period for said sense amplifier and coupled to said communication unit and effective to initiate a communication signal from said communication unit indicating commencement of said refractory period.

2. The medical device according to claim 1 further including sensing test logic that the processor uses during a sensing test to determine a suitable sensitivity for said sense amplifier.

3. The medical device according to claim 2 wherein said sensing test logic is implemented in software executed by said processor.

4. The medical device according to claim 3 wherein said sensing test logic is activated in response to a sensing test start signal from said programmer to begin said sensing test.

5. The medical device according to claim 3 wherein said communication unit is adapted to receive a sensing test start signal from said programmer to begin the sensing test and said communication unit receives signals from said programmer during said refractory period.

6. The medical device according to claim 1, wherein the communication unit is adapted to generate an output signal indicative of the beginning of a refractory period.

7. The medical device according to claim 6, wherein said output signal carries information on the status of the medical device.

8. The medical device according to claim 7, wherein said information includes a sensitivity setting of said sense amplifier.

9. The medical device according to claim 7, wherein said information includes a rate setting of said medical device.

10. A system for electrically stimulating a patient's heart, comprising an implantable medical device, including:

a communication unit;

an electrode adapted to be coupled to the heart;

a sense amplifier electrically coupled to said electrode a processor coupled to said sense amplifier and to said communication unit; said processor controlling a refractory period for said sense amplifier; and a sensing test logic that is used by said processor during a sensing test to determine a suitable sensitivity setting for said sense amplifier, and to initiate a signal from said communication unit indicative of a start of said refractory period; and an external programmer including:
an external communication unit adapted to receive signals from the implantable medical device's communication unit and to transmit signals to the implantable medical device's communication unit during said refractory period.

11. The system according to claim 10 further comprising means for transmitting a status signal from said implantable medical device's communication unit to said external programmer.

12. The system according to claim 10 further including sensing test logic that the processor uses during a sensing test to determine a suitable sensitivity for said sense amplifier.

13. The system according to claim 12 wherein said sensing test logic is implemented in software executed by said processor.

14. The system according to claim 13 wherein said sensing test logic is activated in response to a sensing test start signal from said programmer to begin said sensing test.

15. The system according to claim 13 wherein said communication unit is adapted to receive a sensing test start signal from said programmer to begin the sensing test and said communication unit receives periodic signals from said programmer during said refractory period.

16. The system according to claim 10, wherein said output signal carries information on the status of the medical device.

17. The system according to claim 16, wherein said information includes a sensitivity setting of said sense amplifier.

18. The system according to claim 16, wherein said information includes a rate setting of said medical device.

19. A method for communicating with an implantable medical device, comprising receiving, in said implantable medical device, a start signal to begin a test;

performing said test;

monitoring the electrical activity of a patient's heart determining a refractory period after paced or sensed cardiac event, transmitting a signal to a programmer indicating a beginning of said refractory period; and transmitting signals from said programmer, at a time based on said signal indicating start of said refractory period.

20. The method according to claim 19 wherein said step of transmitting a signal to said programmer further comprises transmitting a status signal from said implantable medical device's communication unit to said external programmer.

21. The method according to claim 19 wherein step of performing said test includes determining a suitable sensitivity for said sense amplifier.

22. The method according to claim 19 further comprising receiving periodic signals from said programmer during said refractory period.

23. The method according to claim 19, wherein the step of transmitting a signal to a programmer comprises transmitting a signal carrying information on the status of the medical device.

24. The method according to claim 23, wherein said information includes a sensitivity setting of said sense amplifier.

25. The method according to claim 23, wherein said information includes a rate setting of said medical device.

* * * * *